United States Patent
Rapaport

(10) Patent No.: US 7,671,038 B1
(45) Date of Patent: Mar. 2, 2010

(54) METHOD OF THERAPEAUTIC TREATMENTS INCLUDING HUMAN IMMUNODEFICIENCY VIRUS (HIV) DISEASE AND OTHER CONDITIONS IN A HUMAN HOST BY ADMINISTERING ADENINE NUCLEOTIDES

(76) Inventor: Eliezer Rapaport, 192 Payson Rd., Belmont, MA (US) 02178

( * ) Notice: Subject to any disclaimer, the term of this patent is extended or adjusted under 35 U.S.C. 154(b) by 0 days.

(21) Appl. No.: 08/131,948

(22) Filed: Oct. 8, 1993

(51) Int. Cl.
*A01N 43/04* (2006.01)
*A61K 31/70* (2006.01)

(52) U.S. Cl. .......................... 514/46; 514/47
(58) Field of Classification Search .................. 514/45, 514/46
See application file for complete search history.

(56) References Cited

U.S. PATENT DOCUMENTS

| | | | | |
|---|---|---|---|---|
| 4,880,918 | A | * | 11/1989 | Rapaport ..................... 514/46 |
| 5,049,372 | A | * | 9/1991 | Rapaport ................... 424/1.77 |
| 5,227,371 | A | * | 7/1993 | Rapaport ..................... 514/46 |
| 2005/0079225 | A1 | | 4/2005 | Rapaport |
| 2009/0215713 | A1 | | 8/2009 | Dagnelie et al. |

OTHER PUBLICATIONS

E Rapaport et al (1989) Proc Natl Acad Sci USA 86: 1662-1666.*
J Lahdevirta et al (1988) Am. J. Medicine 85:289-291.*
Peters et al (1991) British Medical Journal 302: 203-207.*
Hofmann et al., "Restoration of T-Cell function in HIV infection by reduction of intracellular cAMP levels with adenosine analogues," AIDS, pp. 659-664 (1993).*
Hofmann, B., et al., 1993, "Restoration of T-cell function in HIV infection by reduction of intracellular cAMP levels with adenosine analogues", AIDS 7:659-664.*
Hirsch, M. S., and J. Curren, 1990, "Human immunodeficiency viruses: biology and medical aspects", in Virology, Second Edition, B. N. Fields, et al., eds., Raven Press Ltd., pp. 1545-1557.*
Hide, I., et al., 2000, "Extracellular ATP triggers tumor necrosis-factor alpha release from rat microglia", J. Neurochem. 75(3):965-972 (abstract provided).*
Hanley, P. J., et al., 2004, "Extracellular ATP induces oscillations of intracellular Ca2+ and membrane potential and promotes transcription of IL-6 in macrophages", Proc. Natl. Acad. Sci. USA 101(25):9479-9484 (abstract provided).*
Ihara, H., et al., 2005, "ATP-stimulated interleukin-6 synthesis through P2Y receptors on human osteoblasts", Biochem. Biophys. Res. Comm. 326(2):329-334 (abstract provided).*
Inoue, K., 2001, "Independent signaling pathways in ATP-evoked secretion of plasminogen and cytokines from microglia", Drug Develop. Res. 53(2-3):166-171 (abstract provided).*
Singh, G., et al., 1993a, ATP-MgCl2 restores gut absorptive capacity early after trauma-hemorrhagic shock, Am. J. Physiol. 264:R977-R983.*
Rapaport, E., 1990, Mechanisms of anticancer activities of adenine nucleotides in tumor-bearing hosts, Annals N.Y. Academy of Science 603:142-149.*
Wang, P., et al., 1992, ATP-MgCL2 restores renal microcirculation following trauma and severe hemorrhage, Can. J. Physiol. Pharmacol. 70:349-357.*
Singh, G., et al., 1993b, Tumor necrosis factor depresses gut absorptive function, Circulatory Shock 39:279-284.*

\* cited by examiner

*Primary Examiner*—Jeffrey Parkin
(74) *Attorney, Agent, or Firm*—Connolly Bove Lodge & Hutz LLP

(57) ABSTRACT

The administration of adenine nucleotides or adenosine and inorganic phosphate to a human host results in the generation of elevated liver, other organs and red blood cell adenosine 5'-triphosphate (ATP) pools as well as increased levels of ATP and adenosine in the extracellular blood plasma compartment of the blood. The present invention deals with the utilization of the elevated intracellular ATP levels and the elevated extracellular levels of ATP and adenosine for the treatment of a broad spectrum of clinical targets in HIV disease/AIDS and the achievement of decisive therapeutic gains.

22 Claims, No Drawings

METHOD OF THERAPEUTIC TREATMENTS INCLUDING HUMAN IMMUNODEFICIENCY VIRUS (HIV) DISEASE AND OTHER CONDITIONS IN A HUMAN HOST BY ADMINISTERING ADENINE NUCLEOTIDES

TECHNICAL FIELD

The present invention is concerned with treating Human Immunodeficiency Virus infection, and/or Human Immunodeficiency Virus disease, and/or Acquired Immunodeficiency Syndrome related complex, and/or Acquired Immunodeficiency Syndrome, and/or Acquired Immunodeficiency Syndrome with secondary infections, by administering to a human host adenine nucleotides and/or adenosine and inorganic phosphate separately or in combination.

BACKGROUND ART

Acquired immunodeficiency syndrome (AIDS) is a disease resulting from human immunodeficiency virus (HIV) infection. The progression from the initial HIV infection to AIDS-related complex (ARC), AIDS, and AIDS with secondary-infections, which is the end stage of the disease, is long, variable in time and not completely understood (Weiss, R. A., How does HIV cause AIDS? Science 260:1273-1279 [1993]). Another recent review of HIV infection, the course that follows and the pathogenic mechanisms responsible for the clinical outcome is useful for up to date background purposes (Pantaleo, G., Graziosi, C. and Fauci, A. S. The immunopathogenesis of human immunodeficiency virus infection. New England Journal of Medicine 328:327-335 [19993]). A recently published broadly-encompassing article lists all the currently approved anti-HIV agents as well as drugs for the treatment of AIDS and its associated illnesses and secondary infections (Johnson, M. I. and Hoth, D. F., Present status and future prospects for HIV therapies. Science 260:1286-1293 [1993]). This article contains a broad outline of "Current State-of-the-Art Treatment", "Therapies in Development" and "The Future of HIV Therapeutics." An accompanying article of interest dealing with HIV therapeutic (rather than prophylactic) vaccine development is Haynes, B. F. Scientific and social issues of human immunodeficiency virus vaccine development. Science 260:1279-1286 [1993].

All the therapies which were developed or suggested for this disease up to now possess a narrow target, namely, they address a single aspect of the disease. The acknowledged therapies for HIV disease/AIDS are antiretroviral agents such as those approved (AZT or zidovudine, ddI or didanosine and DDC or zalcitabine) along with other antiretroviral agents which are now in clinical trials. The antiretroviral agents are divided into the following categories: reverse transcriptase inhibitors, protease inhibitors, Tat inhibitors, drugs that block viral entry into cells, and nucleic acid-based therapies. The other therapies currently in development are aimed at improving the immune system ("Immune Reconstitution") thus enabling the human host to control HIV infection and its progression. Another general approach to the treatment of AIDS is the development of therapeutic HIV vaccines whereby HIV-infected individuals are treated with viral immunogens designed to boost the anti-HIV immune response and eradicate viral particles along with decreasing the number of virus-infected cells.

U.S. Pat. No. 4,880,918 entitled "Arrest and Killing of Tumor Cells by Adenosine 5'-Diphosphate and Adenosine 5'-Triphosphate" to Rapaport, U.S. Pat. No. 5,049,372 entitled "Anticancer Activities in a Host by Increasing Blood and Plasma Adenosine 5'-Triphosphate (ATP) Levels" to Rapaport, and U.S. Pat. No. 5,227,371 entitled "Utilization of Adenine Nucleotides and/or Adenosine and Inorganic Phosphate for Elevation of Liver, Blood and Blood Plasma Adenosine 5'-Triphosphate Concentrations" to Rapaport, disclose the treatment of cancer by administration of adenine nucleotides to a human host and/or disclose a method to expand organ, blood and blood plasma ATP pools by administration of adenine nucleotides and/or adenosine and inorganic phosphate to a human host.

The role of intracellular ATP as a cellular energy source, a phosphate group donor for phosphorylation reactions and an allosteric regulator of the activities of a variety of cellular proteins has been well-established. Only in the past 10 years have the roles of adenosine and ATP began to emerge as powerful physiological extracellular modulators of intravascular, extravascular and CNS functions, a role which is attracting significant attention within the field of drug development (Williams, M. Purinergic drugs: opportunities in the 1990's. Drug Development Research 28:438-444 [1993]). Adenosine is the endogenous ligand for the A (or $P_1$) type purine receptors affecting mostly cardiovascular and CNS functions, whereas ATP is the ligand for $P_2$ type purine receptors and is now an accepted neurotransmitter (Benham, C. D. ATP joins the fast lane. Nature 359:103-104 [1992]; Edwards, F. A., Gibb, A. J. and Colquhoun, D. ATP receptor-mediated synaptic currents in the central nervous system. Nature 359:144-147 [1992]).

The administration of adenine nucleotides (e.g., ATP, AMP or other adenine nucleotides) into the systemic circulation results in the immediate degradation of the nucleotide to adenosine and inorganic phosphate. This degradation in the vascular bed is followed by incorporation of the adenosine and inorganic phosphate into liver ATP pools (steady state levels) yielding significant expansion of the liver ATP pools, which is followed by an expansion of red blood cell ATP pools. The red blood cells with expanded ATP pools which are produced by this mechanism slowly release micromolar levels of ATP into the blood plasma without undergoing hemolysis, thus achieving elevated steady state extracellular ATP levels, in spite of the catabolic enzymatic activities present intravascularly (Rapaport, E. and Fontaine, J. Anticancer activities of adenine nucleotides in mice are mediated through expansion of erythrocyte ATP pools. Proc. Natl. Acad. Sci. USA 86:1662-1666 [1989]). These elevated levels of ATP inhibit both tumor growth and host weight loss in tumor-bearing murine models. The inhibition of tumor growth proceeds by the receptor-mediated and non-receptor-mediated effects of extracellular ATP on the tumor cell membrane, whereas the inhibition of host weight loss in tumor-bearing hosts is the result of ATP-mediated marked slowdown of hepatic gluconeogenesis and reversal of the depletion of visceral energy stores (Rapaport, E. Mechanisms of anticancer activities of adenine nucleotides in tumor-bearing hosts. Ann. N.Y. Acad. Sci. 603:142-150 [1990]).

Administration of ATP by intravenous infusions at a dose of 50 µg/kg min for at least 48 hours yielded a doubling of blood (red blood cell) ATP levels after 24 hours in advanced cancer patients (most of whom were at stage III B or IV non-small cell lung cancer). Hyperuricemia developed only after at least 48 hours of continuous infusions (Haskell, C. M. and Sanchez-Anaya, D. Hyperuricemia as a complication of ATP: preliminary observation of a phase I clinical trial. ASCO Proceedings 12:435A [1993]) and could be easily dealt with by allopurinol. The elevated blood ATP levels declined within several days after termination of the ATP infusions with a return of total blood ATP levels to their basal levels. In advanced cancer patients with cachexia and malnutrition, the basal blood ATP levels were lower than normal but could be elevated to well above a normal level after ATP infusions.

The mechanisms of expansion of organ ATP levels after administration of ATP proceed by both the increased supply of the major purine precursor for salvage ATP synthesis in cells (adenosine) and the interaction of extracellular ATP with membrane $P_2$-purine receptors which signals an enhanced intracellular ATP synthesis. Most of the expansions of total blood (red blood cell) ATP pools occur due to increased supply of purines to the mature erythrocyte in the hepatic sinusoids, where these purine precursors (mostly adenosine) arise from the increases in turnover of hepatic ATP pools (Rapaport, E. and Fontaine, J. Generation of extracellular ATP in blood and its mediated inhibition of host weight loss in tumor-bearing mice. Biochem. Pharmacol. 38:4261-4266 [1989]). A significant increase in red blood cell ATP pools of the magnitude observed in vivo after ATP administration cannot be obtained in vitro (Rapaport, E. and Fontaine, J. Anticancer activities of adenine nucleotides in mice are mediated through expansion of erythrocyte ATP pools. Proc. Natl. Acad. Sci. USA 86:1662-1666 [1989]).

Adenosine 5'-triphosphate (ATP) infusions useful against metastatic refractory cancers are in Phase I of human clinical trials. The two questions which are being answered by these trials are: 1) is it possible to achieve the degree of elevation of red blood cells, and blood plasma compartment pools of ATP after the administration of ATP to patients as was shown extensively in preclinical murine models, and 2) can the elevated ATP levels in the human host produce the spectrum of anticancer activities demonstrated in experimental animals (Rapaport, E. Mechanisms of anticancer activities of adenine nucleotides in tumor-bearing hosts. Ann. N.Y. Acad. Sci. 603:142-150 [1990]).

A variety of in vitro and in vivo studies have demonstrated several anticancer activities of extracellular (blood plasma compartment) pools of ATP as well as elevated hepatic and red blood cell pools of ATP. These activities are a) cytostatic and cytotoxic effects on the tumor; b) anti-cachexia effects and improvement of hepatic and renal functions; c) modulation of tumoral blood flow; d) antianaemia effects; e) antipain activities; f) improvement in motor functions, performance status; g) improvements in oxygen delivery to peripheral sites; h) enhancement of superoxide anion ($O_2^-$) production by phagocytic cells and i) significant antithrombotic effects in vivo. All of these anticancer activities observed either in experimental animals or in humans after the administration of ATP have been reviewed recently (Rapaport, E. Anticancer activities of adenine nucleotides in tumor-bearing hosts. Drug Development Research 28:428-431 [1993]).

The administration of ATP to tumor-bearing murine hosts was also shown to markedly inhibit host weight loss in a cachectic tumor model and, as importantly, the administration of ATP or other adenine nucleotides was shown to elevate extracellular, blood plasma compartment steady state levels (pools) of ATP. The inhibition of tumor growth and host weight loss were shown not to exhibit a cause and effect relationship in murine models. The cytolytic activity of extracellular ATP against tumor cells is now being proposed by five different groups as accounting for the activity of certain cytolytic T lymphocytes (Filippini, A., Taffs, R. E. and Sitkovsky, M. V. Extracellular ATP in T-lymphocyte activation: Possible role in effector functions. Proc. Natl. Acad. Sci. USA 87:8267-8271 [1990]; Di Virgilio, F., Pizzo, P., Zanovello, P., Bronte, V. and Collavo, E. Extracellular ATP as a possible mediator of cell-mediated cytotoxicity. Immunol. Today 11:274-277 [1990]; Zheng, L. M., Zychlincky, A., Liu, C. C., Ojcius, D. M. and Young, J. D. Extracellular ATP as a trigger for apoptosis or programmed cell death. J. Cell Biol. 112:279-288 [1991]; Steinberg, T. H. and Di Virgilio, F. Cell-mediated cytotoxicity: ATP as an effector and the role of target cells. Curr. Opinion Immunol. 3:71-75 [1991]; Correale, P., Tagliaferri, P., Procopio, A., Coppola, V., Caraglia, M., Celio, L. and Bianco, A. R. ATP is a lymphokine activated killer (LAK) cell cytotoxic factor against colon cancer cells in vitro. Proc. Am. Assoc. Cancer Res. 33:324 [1992]). These cytolytic T lymphocytes release ATP which is stored in their cellular granules, in response to the target cell interaction with a T cell receptor. The extracellular ATP released in the immediate vicinity of the target tumor cell is proposed to deliver the lethal hit. All of these groups demonstrated tumor cell killing by extracellular ATP in a variety of systems.

SUMMARY OF THE INVENTION

Contrary to previously approved therapies and therapies that are known to be under development, the present invention is aimed at the activation of a multitude and a broad spectrum of host functions without directly attacking the virus (HIV) itself. The expansion of organ, red blood cell (total blood) ATP pools and the elevation of extracellular blood plasma adenosine and ATP levels produces the following effects in patients afflicted with AIDS:

1. Improvements of T-cell proliferation and cytotoxicity.
2. Down-regulation of TNF-α and IL-6 synthesis.
3. Improvements in gut absorptive capacity and in the integrity of the intestinal mucosa.
4. Reversal of cachexia-wasting by expansions of organ ATP pools and its mediated inhibition of hypermetabolism.
5. Positive effects on organ function.
6. Cytoprotection during administration of high-dose cytotoxic antiviral agents.

All of these activities will translate into improvements in specific clinical parameters which will ultimately yield survival benefits.

The present invention discloses for the first time a method for treatment of HIV disease/AIDS by administration of adenine nucleotides or adenosine and inorganic phosphate to a human host.

The present invention discloses for the first time that host functions in HIV disease/AIDS can be significantly improved by affecting a broad spectrum of physiological activities, immune and non-immune, with elevated levels of the natural agonists adenosine and ATP.

In particular, the present invention is concerned with a method for treating Human Immunodeficiency Virus infection, and/or Human Immunodeficiency Virus disease, and/or Acquired Immunodeficiency Syndrome related complex, and/or Acquired Immunodeficiency Syndrome, and/or Acquired Immunodeficiency Syndrome with secondary infections, by administering to a human host in need thereof a member selected from the group consisting of: (a) a mixture of adenosine and/or inorganic phosphate; and (b) an adenine nucleotide wherein said adenine nucleotide containing adenosine moiety(ies) and phosphate moiety(ies) and undergoes rapid degradation to adenosine and inorganic phosphate after administration to said host.

BEST AND VARIOUS MODES FOR CARRYING OUT INVENTION

It has been found pursuant to the present invention that a host infected with Human Immunodeficiency Virus and/or suffering from Human Immunodeficiency Virus disease an Acquired Immunodeficiency Syndrome related complex and/or Acquired Immunodeficiency Syndrome and/or acquired Immunodeficiency Syndrome with secondary infections can be treated by being administered a member selected from the group consisting of: (a) a mixture of adenosine and/or inorganic phosphate; and (b) an adenine nucleotide wherein said adenine nucleotide containing adenosine moiety(ies) and phosphate moiety(ies) and undergoes rapid degradation to adenosine and inorganic phosphate after administration to said host.

Examples of such materials are adenosine 5'-monophosphate (AMP), adenosine 5'-diphosphate (ADP), adenosine 5'triphosphate (ATP) and mixtures of adenosine and an inorganic phosphate.

Examples of inorganic phosphates are sodium phosphate, potassium phosphate and phosphoric acid. The pH of any solution employed containing the phosphate is usually adjusted, if necessary, to about 6.0 to about 7.5 by the addition of a base such as sodium hydroxide. Usually, at least about 1 equivalent of phosphate per adenosine is employed, and preferably about 1 to about 3. In addition, pharmaceutically acceptable salt, or metal complexes, or chelates, or liposomes or radio-nuclides of the above compounds can be used.

Preparations containing the above ingredients can be employed in a variety of conventional pharmaceutical preparations. These preparations can contain organic or inorganic material suitable for internal administration. The high solubility of AMP and/or ADP and/or ATP salts and/or adenosine and phosphate salts in isotonic aqueous solutions of sodium chloride enable administration of these agents in the form of injection or infusion of single or multiple doses. The injection or infusion can be intraperitoneal, intravenous, or intra-arterial. AMP and/or ADP and/or ATP and/or adenosine and phosphate salts are also suitable for oral, enteral, or topical application when employed with conventional organic or inorganic carrier substances.

The effective doses are in the range of about 0.1-100 mg/kg of body weight per 24 hours for oral or topical administration, and 0.01-10 mg/kg of body weight per 24 hours for injections. Intravenous, intraperitoneal, or intraarterial infusions of AMP and/or ADP and/or ATP and/or adenosine and phosphate salts in a suitable salt form is preferably administered at a rate of about 0.001-1 mg/kg of body weight per minute. The delivery of these agents can be performed using a variety of drug delivery systems including, but not limited to, pumps or liposomes.

The present invention is based on the presence of purine receptors, the adenosine receptors and the ATP receptors on a variety of cells that affect immune and organ functions in HIV disease/AIDS. The present invention discloses for the first time that host functions in HIV disease/AIDS can be significantly improved by affecting a broad spectrum of physiological activities, immune and non-immune, with elevated levels of the natural agonists adenosine and ATP. The effects of adenosine analogues on a variety of cells is well-established (for a review, see Williams, M. Purinergic drugs: opportunities in the 1990's. Drug Development Research 28:438-444 [1993]). Recently it has also been shown that adenosine analogues that are resistant to metabolic enzymatic activities in mammalian hosts can affect cellular activities and functions that are expected to be highly beneficial to patients with HIV disease/AIDS. Adenosine or ATP are totally unexpected to serve as effectors in these systems in mammalian hosts, because of their well-known metabolic lability which teaches away from the possibility of using them in order to improve immune and non-immune functions in HIV disease/AIDS. As an illustration of the patentability of the present invention, attention is directed to two critical recent reports in this art. The first report (Hofmann, B., Nishanian, P., Nguyen, T., Liu, M. and Fahey, J. L. Restoration of T-cell function by reduction of intracellular CAMP levels with adenosine analogues. AIDS 7:659-664 [1993]) demonstrates that the chemically stable adenosine analogue 2',5'-dideoxyadenosine (ddAdo) can reduce cyclic AMP levels and increase both the proliferative capacity of T-cells to recall antigens and T-cell cytotoxicity in HIV seropositive individuals (without AIDS). These functions are required to be improved for an HIV disease/AIDS treatment to be clinically viable. It is what is often referred to as immune reconstitution. No mention or hint is given in the above cited paper as to the potential use of adenosine itself or ATP for the same purposes. The second report (Parmely, M. J. et al. Adenosine and a related carbocyclic nucleoside analogue selectively inhibit tumor necrosis factor-$\alpha$ production and protect mice against endotoxin challenge. Journal of Immunology 151:389-396 [1993] deals with the use of adenosine and its synthetic analogue for inhibiting tumor necrosis factor-$\alpha$ (TNF-$\alpha$) production from activated macrophages. The requirement for reducing TNF-$\alpha$ and other cytokine levels as part of a successful treatment of HIV disease/AIDS has been established since these cytokines activate immune cells and have a significant stimulating (up-regulation) effect on HIV replication (Poli, G. et al. Tumor necrosis factor $\alpha$ functions in an autocrine manner in the induction of human immunodeficiency virus expression. Proc. Natl. Acad. Sci. USA 87:782-785 [1990]). Although it is stated that adenosine inhibited TNF-$\alpha$ production by activated mouse peritoneal macrophages, adenosine had no effect on RNA levels for TNF-$\alpha$ and most importantly "ADO failed to protect animals against endotoxin lethality, most likely due to the rapid metabolism of the nucleoside in vivo" (bottom of the abstract section). The conclusion to this report (Parmely et al., supra) demonstrates the patentability of the present invention. It states (end of abstract section) that "These results establish ADO and MDL201112 as potent inhibitors of TNF-$\alpha$ biosynthesis and suggest that MDL201112 or similar analogues warrant further study as potential agents for the treatment of endotoxin shock and other diseases in which TNF-$\alpha$ plays an important pathogenic role". Thus, adenosine (and even more so ATP) are totally discounted as potential drugs for HIV disease/AIDS due to their metabolic lability and the widely held notion that neither adenosine nor ATP can be utilized in vivo in a host. The methods disclosed in the present invention provide the art for elevating cellular ATP pools and extracellular adenosine and ATP levels for favorably affecting a wide spectrum of cellular and physiological functions required for the successful treatment of HIV disease/AIDS in human patients.

A variety of unrelated observations as will be discussed below in conjunction with my years of experience with adenine nucleotides and/or mixtures of adenosine and inorganic phosphates has lead me to now suggest the use of the above ingredients for the treatment of Human Immunodeficiency Virus infection, and/or Human Immunodeficiency Virus disease, and/or Acquired Immunodeficiency Syndrome related complex, and/or Acquired Immunodeficiency Syndrome, and/or Acquired Immunodeficiency Syndrome with secondary infections.

Reversal of Cachexia-HIV Wasting Syndrome and Improvement of Organ Function

Mechanisms which were established by the effects of ATP administration to cachectic tumor-bearing murine hosts were recently applied to the treatment of advanced (stage III B and IV) non-small cell lung cancer and other advanced refractory cancers. It is important to note that benefits observed after ATP administration were obtained in spite of the less than favorable schedule of infusions, due to the Phase I nature of the trials, with the questions being addressed dealing mostly with tolerated doses, toxicities, adverse effects, pharmacokinetics and pharmacodynamics. The schedules consisted of continuous 48-96 hour infusions of ATP every fifth week. A doubling in total blood levels of ATP (red blood cell ATP pools) was observed in most patients after 48 hours of infusion (increases from basal levels of 0.9-1 mM to 1.6-2 mM of total blood ATP levels). As was predicted by the murine studies, total blood ATP levels declined over a period of several days after the termination of ATP infusions.

The protocols employed in the present invention as discussed above include infusions of adenine nucleotides or adenosine at levels of 0.001-1.0 milligram per kilogram of body weight per minute, injections of adenine nucleotides or adenosine in amounts of 0.01-10 milligrams per kilogram of body weight per 24 hours, or oral or topical administration of adenine nucleotides or adenosine in amounts of 0.1-100 milligrams per kilogram of body weight per 24 hours. It is beneficial that the levels of ATP or other adenine nucleotides or adenosine should not affect heart rate or mean arterial blood pressure but should produce reductions in systemic vascular resistance and pulmonary vascular resistance with small increases in cardiac output. Hyperuricemia is noticed in infusions that proceed for longer periods than 48 hours, and can be easily prevented by prophylactic use of allopurinol.

Extensive preclinical data suggest that the benefits observed in the initial Phase I trial are a result of the increases in organ and blood ATP levels after the administration of ATP. The most relevant to advanced AIDS are the increases in liver, kidney, splenocytes and gut ATP levels, which in experimental animals have been directly linked to marked improvements in these organs' functions. Several of the improvements related to the increases in red blood cell ATP levels will also contribute to the amelioration of cachexia and positive effects on quality of life parameters in patients suffering advanced HIV infections. These include anti-anaemia effects and improvements in oxygen delivery to peripheral sites. This latter increase in $P_{O_2}$ at 50% $O_2$ saturation ("$P_{50}$, st") is a result of the increases in red blood cell ATP levels which in turn produce significant increases in the erythrocyte 2,3-diphosphoglycerate (DPG) and resulting in a decreased affinity between hemoglobin (Hb) and oxygen, increased tissue oxygen supply because of the facilitated unloading of oxygen from hemoglobin and the final result being an improvement in physical activity.

The ability of infused ATP to restore gut absorptive capacity is extremely significant in regard to the proposed treatment of advanced AIDS with ATP. Since malnutrition is commonly associated with advanced AIDS, total parenteral nutrition is commonly utilized by AIDS patients. Therefore, the ability of intravenously, intramuscularly, or orally administered ATP or other adenine nucleotides or adenosine to rapidly improve gut absorptive capacity and thus favorably affect oral food intake, or to prevent the changes that occur in the intestinal mucosa by improving organ function due to restoration of cellular ATP levels, is expected to have a significant impact on survival of patients with advanced AIDS. The beneficial effects on overall survival of advanced AIDS patients will be augmented by the highly positive effects of ATP expansions on liver and kidney functions.

Downregulation of Cytokines.

The activation of cytokines was demonstrated to have an up-regulatory effect on HIV replication. Cytokines were also shown to become elevated during HIV infections in vitro (Poli, G. et al. Tumor necrosis factor α functions in an autocrine manner in the induction of human immunodeficiency virus expression. Proc. Natl. Acad. Sci. USA 87:782-785 [1990]) or in vivo (Breen, E. C. et al. Infection with HIV is associated with elevated IL-6 levels and production. J. Immunol. 144:480-484 [1990]; Birx, D. L., Redfield, R. R., Tencer, K., Fowler, A., Burke, D. S. and Tosato, G. Induction of interleukin-6 during human immunodeficiency virus infection. Blood 76:2303-2310 [1990]). Whereas TNF-α was shown to possess a direct inductive effect on HIV replication in infected cells, interleukin 6 (IL-6) acts in the activation of B cells in HIV infected individuals. The ability of extracellular adenosine and ATP to reduce cellular synthesis and release of cytokines by monocytes and macrophages is dependent on the presence of membrane adenosine and ATP receptors.

The increase in intestinal blood flow and gut function after administration of adenine nucleotides or adenosine is also expected to contribute to an overall reduction in the levels of circulating cytokines in malnourished advanced AIDS patients, the reason being that those increases in intestinal blood flow and gut function are expected to bring about a repair of the mucosal erosions and reductions in submucosal edemas after administration of adenine nucleotides or adenosine. The improved integrity of the gut mucosa would prevent the low levels of translocation of bacteria and bacterial fragments through the mucosa and their subsequent powerful induction of cytokine synthesis and release.

Improvements in Immune Functions.

The improvements in immune functions by administration of adenine nucleotides or adenosine are of two types: the beneficial effects to the immune system generated by the improvements in organ functions, especially organs which directly affect the immune system such as improvements in liver, kidney, and splenic functions resulting in increased splenocyte IL-2 and IL-3 synthesis; and the recently identified restoration of T-cell function in HIV infection by adenosine which was linked to the adenosine analogues induced reduction in intracellular cAMP levels (Hoffmann, B., Nishinian, P., Nguyen, T., Liu, M. and Fahey, J. L. Restoration of T-cell function in HIV infection by reduction of intracellular cAMP levels with adenosine analogues. AIDS 7:659-664 [1993]). The ability of the administered adenine nucleotides to improve these functions is dependent on the unexpected finding that adenine nucleotides can expand liver, red blood cell and blood plasma (extracellular) ATP pools. The persistent catabolism or enzymatic degradation of the extracellular ATP to adenosine yields elevated extracellular adenosine levels sufficient to activate immune cell purine receptors, and improve immune function. Thus, the common notion that adenosine and ATP are too labile in vivo and only synthetic, chemically and enzymatically stable adenosine or ATP agonists can be utilized for the purpose of immune activation in vivo does not hold in light of the present invention.

The ability of elevated cyclic AMP levels to decrease proliferation and cytotoxicity in normal T-cells has been recognized (Lingk, D. S., Chan, M. A. and Gelfand, E. W. Increased cAMP levels block progression but not initiation of human T-cell proliferation. J. Immunol. 145:449-455 [1990]). Increased cAMP levels were shown to exist in HIV infected peripheral blood mononuclear cells (PBMC) both in vitro after infection of normal PBMC with HIV and in vivo in T-cells isolated from HIV-seropositive individuals (Hoffmann, B., Nishinian, P., Nguyen, T., Liu, M. and Fahey, J. L. Restoration of T-cell function in HIV infection by reduction of intracellular cAMP levels with adenosine analogues. AIDS 7:659-664 [1993]). The mechanisms responsible for the significant inhibitory effects of elevated cAMP on T-cell proliferation and functions are linked to the activity of cAMP-dependent protein kinase (protein kinase A or PKA), which is high in cells from HIV-seropositive subjects. These data therefore suggest to me a mechanism for the decreased function of non-infected T-cells in HIV-seropositive subjects, since less than 1% of CD4 T-cells harbor HIV, yet the significant increases in cAMP levels are observed in cells from HIV-seropositive subjects without AIDS where the majority of the cells are not HIV-infected. Suggested herein as an explanation is immune activation of non-infected cells. The most important aspect of these studies is the ability to restore function by lowering cAMP with adenosine analogues. These analogues are synthetic, chemically and enzymatically stable derivatives of adenosine such as 2',5'-dideoxyadenosine, but not adenosine or ATP themselves.

Protection of Organ Function by Expanded ATP Pools would Enable the Administration of High Doses of Cytotoxic Antiviral Drugs.

Although current clinical utilization of antiviral nucleoside therapy such as zidovudine (AZT) is not associated with severe anaemia and severe hepatotoxicity that would render its use prohibitive in asymptomatic HIV infection, hematologic as well as hepatic toxic effects are observed to some extent, especially with high doses of zidovudine (Volberding, P. A. et al. Zidovudine in asymptomatic human immunodeficiency virus infection. N. Engl. J. Med. 322: 941-949 [1990]). However, the earlier trials of AZT that included subjects with advanced AIDS who were anemic before the initiation of therapy and whose nutritional status was poor demonstrated significant hematological toxicities attributed to AZT (Richman, D. D. et al. The toxicity of azidothymidine (AZT) in the treatment of patients with AIDS and AIDS-related complex. N. Engl. J. Med. 317:192-197 [1987]). Serious anaemia or neutropenia during AZT treatment of advanced AIDS patients was significant, although AZT did not seem to severely affect hepatic, renal, or gastrointestinal absorptive functions in a large fraction of advanced AIDS patients. The present and future development of cytotoxic anti-HIV therapies (Johnston, M. I. and Hoth, D. F. Present status and future prospects for HIV therapeutics. Science 260:1286-1293 [1993]) which are likely to lead to adverse hepatic, renal, or gastrointestinal absorptive functions provide the incentive for the development of ATP as a protective agent. As discussed hereinabove, the demonstrated ability of administered ATP to act in expanding organ and total blood ATP pools is responsible for the improved organ and red blood cell functions. Function is directly related to ATP levels during adverse conditions, and extracellularly administered ATP acts by interacting with cell membrane $P_2$-purine receptors in stimulating, through an extracellular signal, cellular purine nucleotide synthesis as well as providing a salvage precursor, adenosine, for this synthesis.

The data discussed above lead me to assert the following conclusions: administration of adenine nucleotides or adenosine and inorganic phosphate to a patient suffering from HIV disease/AIDS will result in significant increases in organ and red blood cell ATP pools and as a result of the expanded red blood cell ATP pools, elevated levels of ATP and its catabolic product adenosine will be produced in the extracellular blood plasma compartment. These elevated extracellular ATP and adenosine levels are produced due to the release of micromolar amounts of ATP from red blood cells into the blood plasma in a non-hemolytic process and the constant degradation of ATP to adenosine by enzymatic activities present in the vascular bed. The therapeutic targets that will be achieved by the present invention for the treatment of HIV disease/AIDS are reversal of cachexia, improvements in performance status and organ function, down-regulation (inhibition of synthesis and/or release) of cytokines, improvements in immune cell function (immune reconstitution), and—due to the noted cytoprotection achieved by expansions of cell and organ ATP pools—combination of administration of adenine nucleotides or adenosine and inorganic phosphate along with or followed by antiviral cytotoxic drugs.

Having thus described my invention, what I claim as new and desire to secure by Letters Patent is:

1. A method for suppressing cachexia-wasting, and/or improving skeletal muscle functions, and/or slowing cancer progression by administering to a human host in need thereof a member selected from the group consisting of: (a) adenosine 5'-monophosphate; (b) adenosine 5'-diphosphate; (c) adenosine 5'-triphosphate; and mixtures thereof, pharmaceutically acceptable salt thereof, or chelate thereof, or metal complex thereof, or liposome thereof.

2. The method of claim 1 wherein said member is administered to a human host as pharmaceutically acceptable salt thereof, or chelate thereof, or metal complex thereof, or liposome thereof.

3. The method of claim 1 wherein adenosine 5'-monophosphate is administered to said host.

4. The method of claim 1 wherein adenosine 5'-triphosphate is administered to said host.

5. The method of claim 1 wherein skeletal muscle functions are improved in a human host by administering to said host adenosine 5'-monophosphate, and/or adenosine 5'-triphosphate.

6. The method of claim 1 wherein cachexia-wasting is treated in a human host by administering to said host adenosine 5'-monophosphate, and/or adenosine 5'-triphosphate.

7. The method of claim 1 wherein cancer progression is slowed in a human host by administering to said host adenosine 5'-monophosphate, and/or adenosine 5'-triphosphate.

8. The method of claim 1 wherein the amount of adenosine 5'-monophosphate, and/or adenosine 5'-diphosphate, and/or adenosine 5'-triphosphate; is about 0.001-1 mg/kg of body weight per minute and said administering is by infusion.

9. The method of claim 1 wherein the amount of adenosine 5'-monophosphate; and/or adenosine 5'-diphosphate; and/or adenosine 5'-triphosphate is about 0.01-10 mg/kg of body weight per 24 hours and said administering is by injection.

10. The method of claim 1 wherein the amount of adenosine 5'-monophosphate; and/or adenosine 5'-diphosphate; and/or adenosine 5'-triphosphate; is about 0.1-100 mg/kg of body weight per 24 hours and said administering is oral or topical.

11. A method for suppressing cachexia-wasting, and/or improving skeletal muscle functions by administering to a human host suffering from HIV Disease a member selected from the group consisting of: (a) adenosine 5'-monophosphate; (b) adenosine 5'-diphosphate; (c) adenosine 5'-triphosphate; and mixtures thereof, pharmaceutically acceptable salt thereof, or chelate thereof, or metal complex thereof, or liposome thereof.

12. The method of claim 11 wherein said member is administered to a human host as pharmaceutically acceptable salt thereof, or chelate thereof, or metal complex thereof, or liposome thereof.

13. The method of claim 11 wherein adenosine 5'-monophosphate is administered to said host.

14. The method of claim 11 wherein adenosine 5'-triphosphate is administered to said host.

15. The method of claim 11 wherein skeletal muscle functions are improved in a human host by administering to said host adenosine 5'-monophosphate, and/or adenosine 5'-triphosphate.

16. The method of claim 11 wherein cachexia-wasting is treated in said human host by administering to said host adenosine 5'-monophosphate, and/or adenosine 5'-triphosphate.

17. The method of claim 11 wherein cancer progression is slowed in a human host by administering to said host adenosine 5'-monophosphate, and/or adenosine 5'-triphosphate.

18. The method of claim 11 wherein the amount of adenosine 5'-monophosphate; and/or adenosine 5'-diphosphate; and/or adenosine 5'-triphosphate; is about 0.001-1 mg/kg of body weight per minute and said administering is by infusion.

19. The method of claim 11 wherein the amount of adenosine 5'-monophosphate; and/or adenosine 5'-diphosphate; and/or adenosine 5'-triphosphate; is about 0.01-10 mg/kg of body weight per 24 hours and said administering is by injection.

20. The method of claim 11 wherein the amount of adenosine 5'-monophosphate; and/or adenosine 5'-diphosphate; and/or adenosine 5'-triphosphate; is about 0.1-100 mg/kg of body weight per 24 hours and said administering is oral or topical.

21. The method of claim 1 wherein said administering provides for suppressing cachexia-wasting, and/or improving skeletal muscle functions, and/or slowing the progression of cancer.

22. The method of claim 11 wherein said administering provides for suppressing cachexia-wasting, and/or improving skeletal muscle functions, and/or slowing the progression of cancer.

* * * * *